US012114983B2

(12) United States Patent
Yang et al.

(10) Patent No.: US 12,114,983 B2
(45) Date of Patent: Oct. 15, 2024

(54) APPARATUS AND METHOD FOR CARDIAC SIGNAL PROCESSING, MONITORING SYSTEM COMPRISING THE SAME

(71) Applicant: INDUSTRY ACADEMIC COOPERATION FOUNDATION OF YEUNGNAM UNIVERSITY, Gyeonsan-si (KR)

(72) Inventors: Jong Ryul Yang, Gyeongsan-si (KR); Ju Yeon Kim, Daegu (KR)

(73) Assignee: Industry Academic Cooperation Foundation Of Yeungnam University, Gyeonsan-Si (KR)

( * ) Notice: Subject to any disclaimer, the term of this patent is extended or adjusted under 35 U.S.C. 154(b) by 831 days.

(21) Appl. No.: 17/256,815

(22) PCT Filed: Nov. 6, 2020

(86) PCT No.: PCT/KR2020/015443
§ 371 (c)(1),
(2) Date: Dec. 29, 2020

(87) PCT Pub. No.: WO2021/096162
PCT Pub. Date: May 20, 2021

(65) Prior Publication Data
US 2021/0290139 A1    Sep. 23, 2021

(30) Foreign Application Priority Data

Nov. 13, 2019  (KR) .................. 10-2019-0144981
Dec. 20, 2019  (KR) .................. 10-2019-0172336
Nov. 4, 2020   (KR) .................. 10-2020-0145736

(51) Int. Cl.
A61B 5/318   (2021.01)
A61B 5/00    (2006.01)
(Continued)

(52) U.S. Cl.
CPC .......... *A61B 5/327* (2021.01); *A61B 5/02405* (2013.01); *A61B 5/352* (2021.01);
(Continued)

(58) Field of Classification Search
CPC ..... A61B 5/327; A61B 5/352; A61B 5/02405; A61B 5/7267; G16H 50/20; G06N 3/08
See application file for complete search history.

(56) References Cited

U.S. PATENT DOCUMENTS 11,010,642 B2 *  5/2021  Soni .................. G06V 10/454
11,534,136 B2 * 12/2022  Funka-Lea ............ A61B 90/36
(Continued)

FOREIGN PATENT DOCUMENTS

KR  10-2012-0000398 A    1/2012
KR     101649445 B1     8/2016
(Continued)

OTHER PUBLICATIONS

S. Haradal, H. Hayashi and S. Uchida, "Biosignal Data Augmentation Based on Generative Adversarial Networks," 2018 40th Annual International Conference of the IEEE Engineering in Medicine and Biology Society (EMBC), Honolulu, HI, USA, 2018, pp. 368-371, doi: 10.1109/EMBC.2018.8512396. (Year: 2018).*
(Continued)

*Primary Examiner* — Eric D. Bertram
(74) *Attorney, Agent, or Firm* — Osha Bergman Watanabe & Burton LLP

(57) ABSTRACT

Apparatus for cardiac signal processing includes an input signal processor for receiving cardiac signals collected in time series by a sensor, and extracting and processing only signals necessary for diagnosis; a signal processor for generating diagnostic data by signal-processing the diagnostic data of the input signal processor to ensure accuracy of bio diagnosis analysis for an actual subject to be measured; and
(Continued)

an output signal processor for outputting the diagnostic data to diagnose a condition of the subject to be measured.

10 Claims, 10 Drawing Sheets

(51) Int. Cl.
    *A61B 5/024*     (2006.01)
    *A61B 5/327*     (2021.01)
    *A61B 5/352*     (2021.01)
    *G06N 3/08*     (2023.01)
    *G16H 50/20*     (2018.01)

(52) U.S. Cl.
    CPC ............. *A61B 5/7267* (2013.01); *G06N 3/08* (2013.01); *G16H 50/20* (2018.01)

(56) References Cited

U.S. PATENT DOCUMENTS

| | | | |
|---|---|---|---|
| 2017/0156678 A1 | 6/2017 | Lim et al. | |
| 2019/0046113 A1* | 2/2019 | Nikolic | G06F 18/24133 |
| 2019/0223819 A1* | 7/2019 | Mansi | G06T 15/205 |
| 2020/0134876 A1* | 4/2020 | Park | G06V 10/764 |
| 2020/0204546 A1* | 6/2020 | Li | G06V 40/15 |
| 2020/0342968 A1* | 10/2020 | Avinash | G16H 15/00 |
| 2021/0035340 A1* | 2/2021 | Wang | G06V 10/82 |
| 2021/0035341 A1 | 2/2021 | Lee et al. | |
| 2021/0125331 A1* | 4/2021 | Sun | G06T 7/143 |

FOREIGN PATENT DOCUMENTS

| | | |
|---|---|---|
| KR | 20190056858 A | 5/2019 |
| KR | 20190103926 A | 9/2019 |
| KR | 102033484 B1 | 10/2019 |

OTHER PUBLICATIONS

Zhu F, Ye F, Fu Y, Liu Q, Shen B. Electrocardiogram generation with a bidirectional LSTM-CNN generative adversarial network. Sci Rep. May 1, 2019;9(1):6734. doi: 10.1038/s41598-019-42516-z. PMID: 31043666; PMCID: PMC6494992. (Year: 2019).*

English translation of International Search Report issued in corresponding International Application No. PCT/KR2020/015443, mailed Mar. 2, 2021 (3 pages).

Office Action issued in corresponding Korean Patent Application No. 10-2020-0145736, issued on May 15, 2022 (7 pages).

Kim, Min-Gu, "A Study on User Recognition System Based on Ensemble Convolutional Neural Networks Using Synthetic Electrocardiogram Generation," Chosun University, Aug. 23, 2019, with English Abstract (86 pages).

Office Action issued in related Korean application No. 10-2023-0069834, dated Jul. 1, 2023, with English translation (10 pages).

* cited by examiner

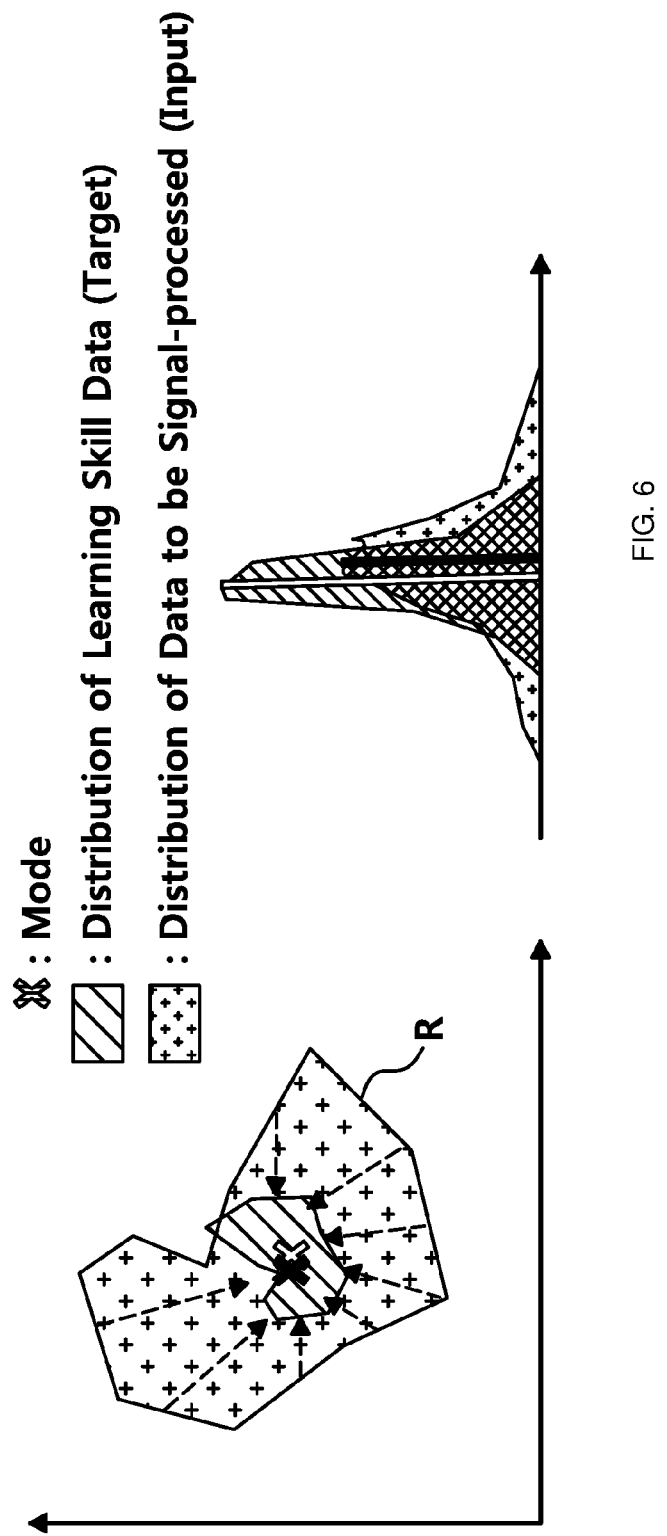

APPARATUS AND METHOD FOR CARDIAC SIGNAL PROCESSING, MONITORING SYSTEM COMPRISING THE SAME

TECHNICAL FIELD

The present invention relates to apparatus and method for cardiac signal processing, and in particular, a cardiac signal processing apparatus and method capable of accurately analyzing the condition of a subject to be measured by using a sensor signal that has no environmental constraints compared to a method using a general electrocardiogram, and a monitoring system including the same.

BACKGROUND ART

The cardiac signal, which is important biometric information reflecting the condition of the body, has periodic characteristics due to homeostasis, but it has variability within a certain range, therefore it is important to secure the accuracy of the signal for analysis of the heart rate variability that interprets the variability.

There are various methods for testing or checking the cardiac signal, among which there is an electrocardiogram-based method. The results of these electrocardiograms can provide a lot of information. For example, it is possible to predict the possibility of driver's drowsiness or motion sickness, or to know the drinking condition, and to know the abnormal condition of the heart rate. In other words, it is possible to predict various biological responses.

However, although it is possible to extract a lot of information from an electrocardiogram, because of many limitations in the measurement method that should directly contact the skin, it can be inferred that the measurement method cannot easily applied to various applications. Therefore, various processing methods were sought to process the condition analysis or diagnosis of the subject to be measured while reducing the influence of external interference and location. As an example of such processing method, the method of using a radar signal that can check the heart rate or respiration rate per minute was discussed. This is because, if the accuracy of biometric information similar or equal to the information extracted from the electrocardiogram is obtained from the radar signal, it is possible to predict various biometric reactions in the same way as using the electrocardiogram-based method while solving the problem of the measurement method.

However, it is impossible to convert the radar signal into an electrocardiogram signal. Because the electrocardiogram measures an electric signal while the radar signal measures motion itself, the two signals have fundamentally different data types, and therefore, the signal extraction method is inevitably different.

Nevertheless, if various bio-diagnosis that can be provided by an electrocardiogram is possible by using a radar signal that can be measured in a non-contact state, analysis and condition diagnosis using cardiac signals can be efficiently performed. That is, if it is possible to detect biometric information with high accuracy while acquiring a cardiac signal remotely, it will be possible to utilize biometric response prediction such as an electrocardiogram-based method in various applications that could not be utilized due to the limitation of the measurement method in the prior art.

SUMMARY

Technical Problem

Accordingly, it is an object of the present invention to provide a cardiac signal processing apparatus and method for analyzing and diagnosing the condition of the subject to be measured remotely while improving the accuracy of the bio-signal, by processing a signal to be analyzed (i.e., a cardiac signal) extracted from a contact or non-contact type sensor.

Another object of the present invention is to learn a cardiac signal detected by a sensor or a signal with enhanced characteristics of the cardiac signal.

Another object of the present invention is to improve the accuracy of biometric diagnosis by applying a signal processing method using a generative adversarial network algorithm.

Another object of the present invention is to provide a cardiac signal processing apparatus and method for improving the accuracy of biodiagnosis analysis by minimizing the influence of external interference by detecting biometric information by restoring a distorted signal included in a sensor signal.

Another object of the present invention is to provide a monitoring system that monitors condition of a driver or a patient by using a cardiac signal even in an environment with movement and external influences.

Solution to Problem

Apparatus for cardiac signal processing comprising: an input signal processor that receives a cardiac signals collected in time series by a sensor and extracts and processes only signals necessary for diagnosis; a signal processor for generating diagnostic data by signal-processing the diagnostic data of the input signal processor to ensure accuracy of bio diagnosis analysis for an actual subject to be measured; and an output signal processor for outputting the diagnostic data to diagnose a condition of the subject to be measured.

The signal processor, uses a generative adversarial network.

The generative adversarial network comprises: a generator network that generates false data identical to the diagnostic data by using a generation vector; and a discriminator network which performs learning until the diagnostic data and the false data cannot be discriminated by receiving the false data and the diagnostic data.

The input signal processor, extracts input parameters from time series data, or processes input signals by configuring them in a matrix form for a multidimensional input structure.

The output signal processor, extracts an analysis parameter from the diagnostic data to analyze a heart rate variability, or processes it into a waveform similar to an electrocardiogram signal and outputs it.

The analysis parameters are, extracted after signal processing by the generative adversarial network or, recovery of lost and distorted diagnostic data.

Apparatus for cardiac signal processing comprising: an input unit for receiving a sensor signal collected in time series by a sensor; a signal generator for generating a waveform or function similar in shape to a cardiac signal by enhancing characteristics of the sensor signal; a data processor for processing data necessary for condition diagnosis by using the generated waveform or function; a signal processor for comparing and learning until it is determined that the processed data of the data processor and a reference data are the same; an output unit for outputting the signal-processed diagnostic data; and a diagnosis unit for performing diagnosis by the output diagnostic data.

The signal processor, uses a generative adversarial network.

Apparatus for cardiac signal processing comprising: sensors for sensing a cardiac-related signal; and a neural network learning unit that compares the processed data using the sensed cardiac signal or a signal with enhanced characteristics of the cardiac signal with previously provided reference data, and learns until it is determined that the processed data and the reference data are identical to each other, wherein the condition is diagnosed with the learned diagnostic data.

The signal with enhanced characteristics of the cardiac signal is a waveform or function signal that has a shape similar to that of a cardiac signal.

The neural network learning unit is a generative adversarial network that continuously compares two data until they are the same.

A method for cardiac signal processing, in a method of performing a condition diagnosis of a subject to be measured by using a cardiac signal, a sensing step in which a sensor senses a cardiac signal of the subject to be measured; an extracting step for extracting only diagnostic data necessary for diagnosis from the sensed cardiac signal; a signal processing step for signal-processing the diagnostic data to convert to the diagnostic data improved to ensure accuracy of biometric information at a level capable of diagnosing a condition; and a diagnosis step for diagnosing a condition of a subject to be measured through the converted diagnostic data.

The signal processing step, generates false data of the diagnostic data by using a generation vector, the diagnostic data repeatedly learns and performs the false data until it becomes similar to the level of the diagnostic data. The learning of the false data refers to learning features of the reference data.

The level of the diagnostic data is the accuracy of biometric information of the data is predictable as in an electrocardiogram-based method.

The signal processing step, uses a generative adversarial network algorithm.

The diagnosis step, comprises detecting an analysis parameter for diagnosis of the condition from the diagnostic data of which lost and distorted information is restored, and determines the condition of the subject to be measured by using the detected analysis parameter.

The extracting step, further comprises: generating a waveform or a function signal for enhancing characteristics of a cardiac signal from the sensed cardiac signal; and a step of generating processed data by using the waveform or function signal, and wherein the signal processing step is comparing the processed data and reference data until they are the same.

The reference data is a data having biometric information accuracy of the level collected by a contact sensor.

A monitoring system comprising: an input signal processor for receiving cardiac signals collected in time series by a sensor and extracting and processing only signals necessary for diagnosis; a signal processor for converting the diagnostic data of the input signal processor into an improved signal by using a generative adversarial network to ensure accuracy of condition diagnosis for an actual subject to be measured; and a monitoring unit for monitoring the condition of the subject to be measured by using a diagnostic data by the signal processor.

The diagnostic data is a cardiac signal measured by a contact sensor or a non-contact sensor, and wherein the noise processing, restoration of loss or distortion of the diagnostic data, securing accuracy of biometric information are converted by using the signal processor.

Effects of the Invention

According to the apparatus and method for cardiac signal processing, and monitoring system of the present invention as described above, a cardiac signal of a subject measured through a sensor is signal-processed by using a generative adversarial network algorithm, and used for condition diagnosis. Therefore, it is possible to remove noise, and to restore loss and distortion from the signal measured by the contact or non-contact sensor, thereby reducing the effect of external interference.

In addition, because diagnostic data that is signal-processed by the generative adversarial network algorithm can restore and use the biometric information from the signal measured by the non-contact sensor being improved to the accuracy level of the contact sensor, it can be used in various application fields by solving spatial constraints.

BRIEF DESCRIPTION OF DRAWINGS

FIGS. 5 and 6 are exemplary diagrams of diagnostic data finally output according to the present invention.

METHOD FOR CARRYING OUT THE INVENTION

Figure 1:
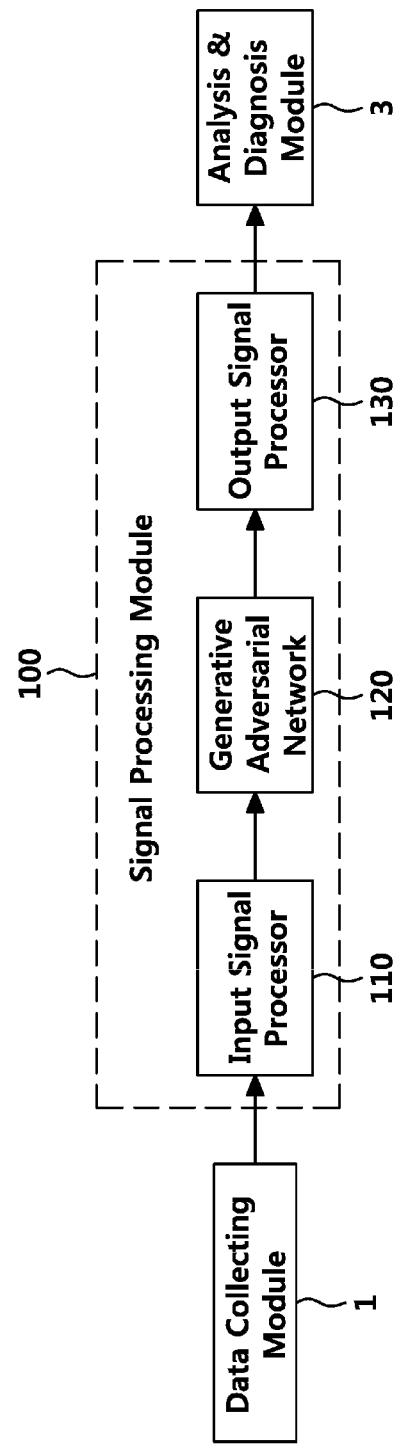
FIG. 1 is a configuration diagram of a cardiac signal processing apparatus according to an embodiment of the present invention.

Objects and effects of the present invention, and technical configurations for achieving them will become apparent with reference to embodiments described below in detail together with the accompanying drawings. In describing the present invention, if it is determined that a detailed description of a known function or configuration may unnecessarily obscure the subject matter of the present invention, a detailed description thereof is omitted.

In addition, terms to be described are terms defined in consideration of functions in the present invention and may vary according to the intention or custom of users or operators.

However, the present invention is not limited to the embodiments disclosed below, and may be implemented in various different forms. The present embodiments are provided only to complete the disclosure of the present invention and to fully inform the scope of the invention to those of ordinary skill in the art to which the present invention belongs, and the present invention is defined by the scope of the claims. Therefore, the definition should be made based on the contents throughout this specification.

Hereinafter, the present invention is described in more detail based on the embodiments illustrated in the drawings.

FIG. 1 is a block diagram illustrating a cardiac signal processing apparatus according to an embodiment of the present invention, and includes a data collection module 1, a signal processing module 100, and an analysis and diagnosis module 3 as illustrated.

The data collection module 1 collects cardiac-related signals in time series. The cardiac-related signals may be, for example, an electrocardiogram signal that can be measured by a contact sensor or a signal collected by a radar sensor that can be measured by a non-contact sensor (referred to as a 'radar signal'). The present embodiment is described by using characteristic signals related to biometric information extracted from the ECG signal having a distorted part. That is, because it shows that the accuracy of biometric information can be secured by signal-processing the cardiac signal measured from the contact and non-contact sensors, and it is related to the features proposed by the present invention.

The distorted signal is used in the present embodiment because it can confirm that the accuracy of biometric information can be secured. That is, the characteristic signal extracted from the cardiac signal collected by the sensor can be restored to enable condition prediction, and the accuracy of biometric information with the level of the signal collected by the contact sensor can be obtained from the signal collected by the non-contact sensor. Therefore, signal processing is required to remove noise, and to restore loss and distortion from the collected cardiac signals, and to ensure accuracy of biometric information. For this purpose, a signal processing module 100 is provided in this embodiment.

The signal processing module 100 includes an input signal processor 110, a generative adversarial network 120 (GAN), and an output signal processor 130. The input signal processor 110 serves to extract only characteristic signals necessary for condition diagnosis from the sensor signals collected by the data collection module 1. For example, the characteristic signal may be a heart rate-related peak position and a time interval between peaks in a radar signal, and in an electrocardiogram signal, it may be a QR section, an RS section, and an RR section signal extracted from the 'PQRST' waveform. In addition, the signal extracted from the sensor signal by the input signal processor 110 needs to improve the accuracy of biometric information similar to the level of the ECG signal. This is because if the accuracy is low, it is difficult to diagnose and predict the condition of the subject to be measured.

The generative adversarial network 120 is provided to improve the accuracy of biometric information of the sensor signal. The generative adversarial network 120 has two neural networks: the discriminator network 122 and the generator network 124. The discriminator network 122 receives the actual data of the input signal processor 110 with the false data (generator data) generated by the generator network 124 and compares them to determine whether it is actual or false, and the generator network 124 serves to generate false data similar to the actual data that already exists.

Figure 2:
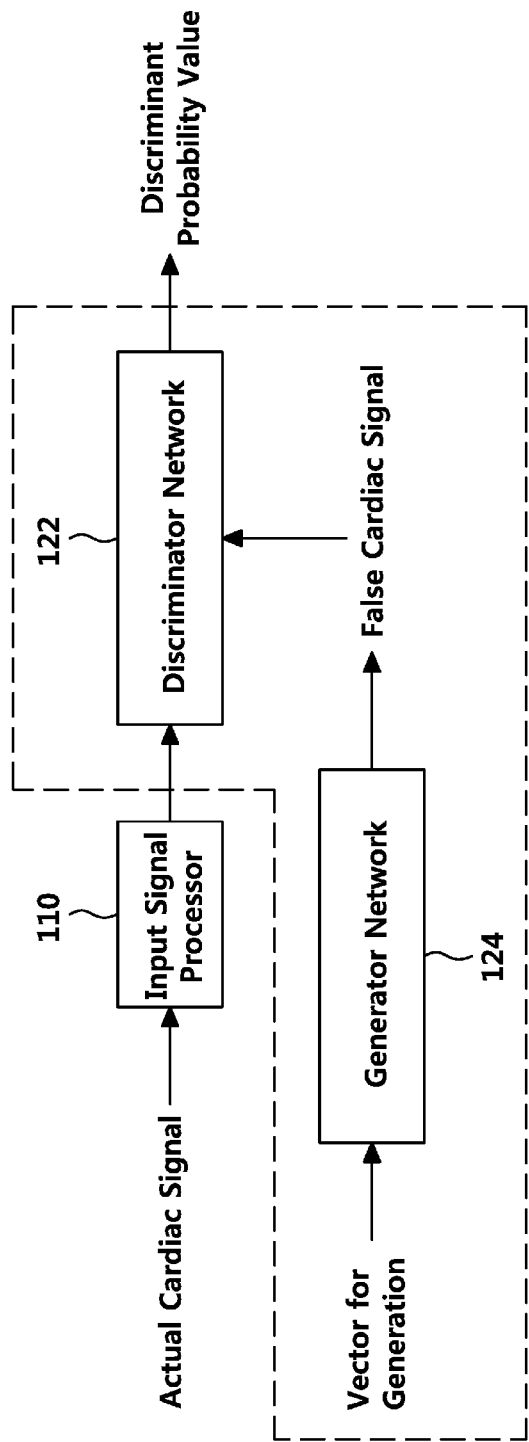
FIG. 2 is an internal configuration diagram of the generative adversarial network of FIG. 1.

Therefore, the generative adversarial network 120 in the present invention generates biometric information results of the level of an actual ECG signal based on sensor signal through learning. In other words, in FIG. 2, the actual cardiac signal and the false cardiac signal learns from each other, to the extent that it is impossible to discriminate between the actual cardiac signal and the false cardiac signal.

In addition, such a generative adversarial network 120 may change various design parameters for balanced learning between the generator and the discriminator and performance improvement. Parameters are batch size, epoch size, layer design, and input size.

Referring back to FIG. 1, the output signal processor 130 serves to output diagnostic data which is signal-processed by the generative adversarial network 120 for diagnosis of the condition. Here, the output signal processor 130 also performs a function of extracting related parameters from the diagnostic data based on a method such as heart rate variability analysis for diagnosis of the condition. That is, because lost or distorted information can be restored by using the generative adversarial network, and parameters with improved accuracy can be extracted from the restored diagnostic data, in the previous step of the output signal processor 130. In addition, it also serves to process the extracted information into a signal waveform to have a waveform of the ECG signal.

Figure 3:
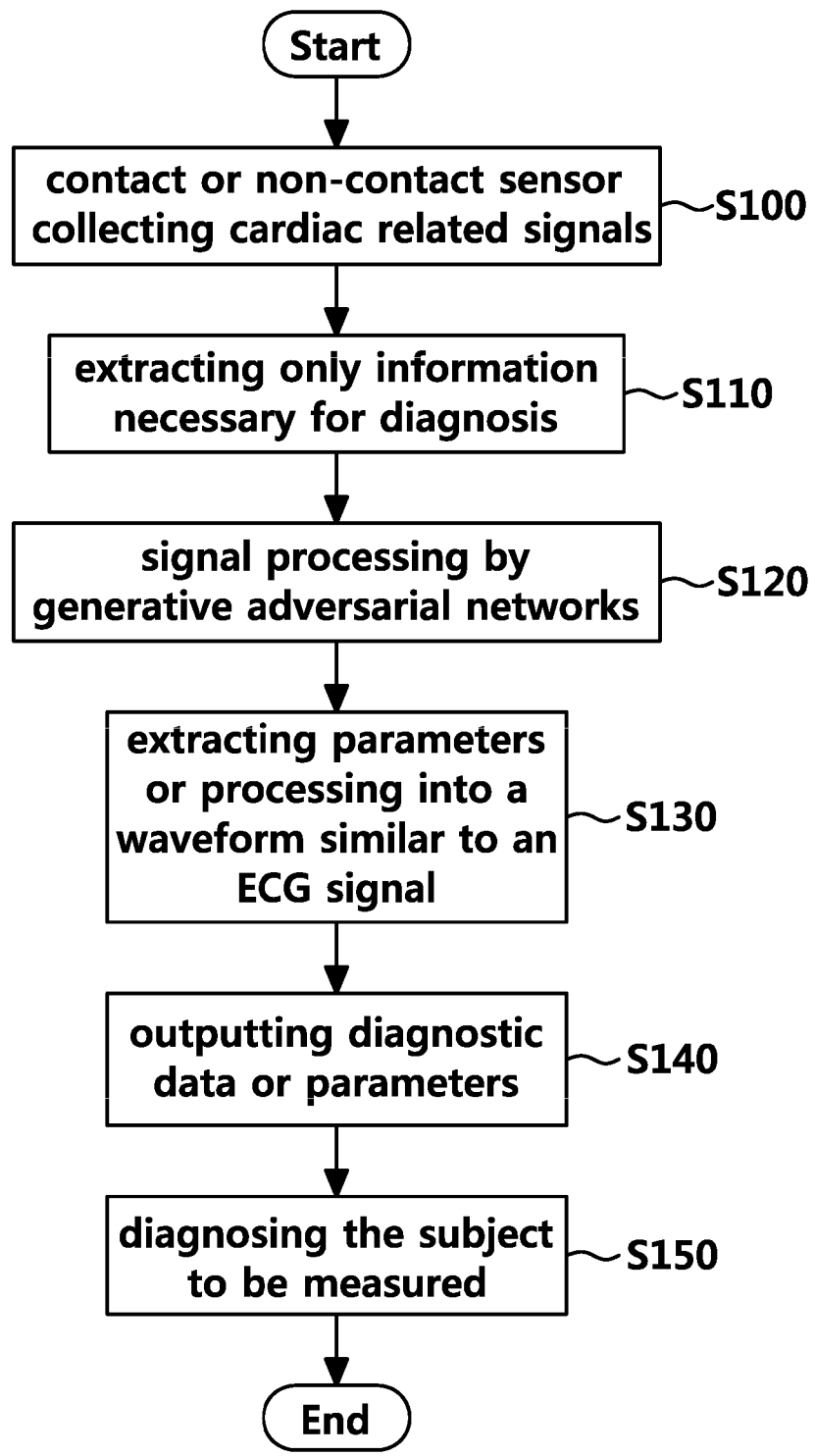
FIG. 3 is a flowchart illustrating a cardiac signal processing method according to an embodiment of the present invention.

Next, a process of analyzing and diagnosing the condition of a subject to be measured by using the cardiac signal processing apparatus configured as described above is described with reference to the flowchart of FIG. 3.

The data collection module 1 may be at least one measurement sensor, and is attached in the form of contact to a location where a signal can be collected from the subject to be measured or the subject, or is installed in the appropriate location so that it can measure around the heart and chest cavity of the subject to be measured in a non-contact state such as a radar sensor. These measurement sensors collect cardiac related signals of the subject to be measured in time series (S100). Because the sensor signal is signal-processed when the accuracy of the biometric information is low enough to make it impossible to diagnose the condition, the sensor signal is sensed in the form of, for example, the 'R' area of FIG. 6. These signals are collected in the form of time series data expressed as a function of time over a certain period of time.

The input signal processor 110 extracts only information necessary for actual diagnosis from the time series data (S110). For example, it may be biometric information such as a heart rate or a time interval between heart rates. Because such information is included in the radar signal in addition to the electrocardiogram signal, it can be extracted. Of course, radar signals also contain other biometric information and noise.

Figure 4A:
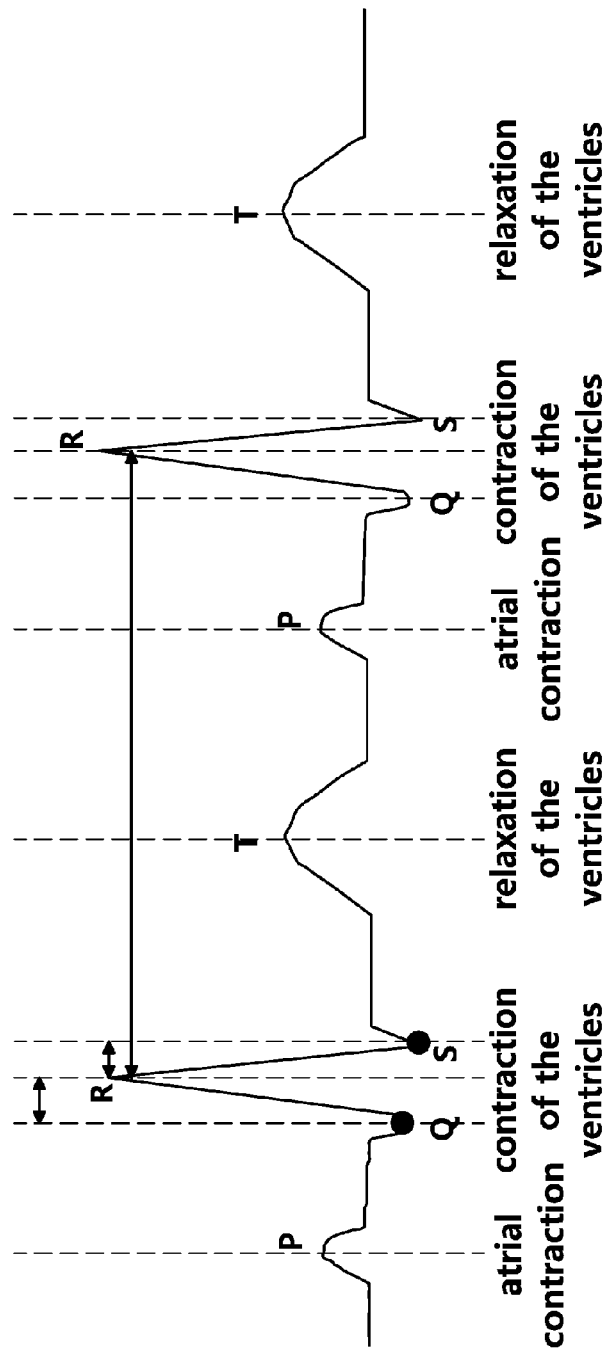
FIG. 4 is an exemplary view of processing an input signal in a method for processing a cardiac signal according to the present invention.
Figure 4B:
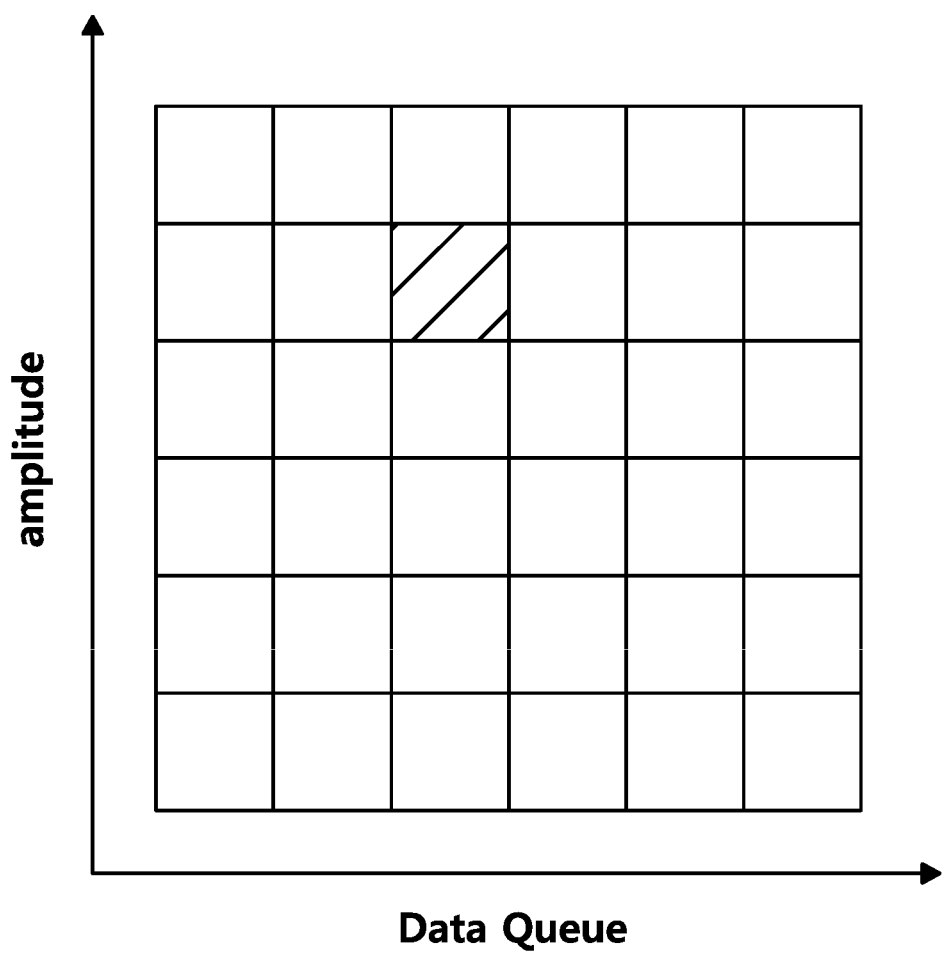

Referring to FIG. 4, an example illustrates the input signal processor 110 extracting only necessary information from time series data. According to the figure, a specific signal section such as a QR section, an RS section, and an RR section can be extracted from the PQRST waveform of the ECG signal, or be stored in a data queue for processing. In addition, data such as heart rate or time interval between heart rates can be extracted from radar signals or processed being stored in a data queue. By using these various parameters, it is possible to diagnose an abnormal heart condition or current condition of the subject to be measured. Meanwhile, according to the present embodiment, the input signal processor 110 may extract an input parameter from time series data as in FIG. 4A or may process an input signal by configuring in a matrix form for a multidimensional input structure as illustrated in FIG. 4B.

The data extracted and processed by the input signal processor 110 is diagnostic data extracted from a signal that is difficult to perform condition diagnosis. Therefore, the accuracy is not higher than that of the ECG data, and therefore it is necessary to perform signal processing to obtain the accuracy level of the ECG data.

The generative adversarial network 120 learns with two neural networks, the discriminator network 122 and the generator network 124 (S120) as already known. That is, the generator network 124 generates false data similar to the diagnostic data extracted and processed by the input signal processor 110 by using the generation vector, and the discriminator network 122 receive the diagnostic data and the false data to perform learning. According to this learning, the generative adversarial network 120 can signal-process and convert the diagnostic data up to a level of ECG data that enables diagnosing and predicting the actual condition.

The generative adversarial network 120 as described above is used because it is possible to diagnose a condition by analyzing the variability that affects the accuracy of biometric information as well as the periodic characteristics of the cardiac signal. Accordingly, a sensor signal having low biometric information accuracy is signal-processed by using the generative adversarial network 120 to improve to the level of the ECG signal.

The generative adversarial network 120 learns to the extent that the false data provided by the generator network 124 is indistinguishable from the diagnostic data, and thus, the output of the generative adversarial network 120 provides diagnostic data with improved accuracy to the level of ECG data.

The output signal processor 130 extracts an analysis parameter from the diagnostic data or processes and restores it in a waveform shape similar to an electrocardiogram signal in order to output condition diagnosis information (S130). That is, additional information is detected for more various condition diagnosis from the diagnostic data with improved accuracy of biometric information by restoring lost or distorted signal through the generative adversarial network 120. Here, the additional information may be a parameter based on heart rate variability analysis verified from ECG data.

As a result of such a detection, the output signal processor 130 outputs the diagnostic data or parameter (S140), and the analysis and diagnostic module 3 may diagnose the condition of the subject to be measured based on the diagnostic data or parameter. (S150).

Figure 5A:
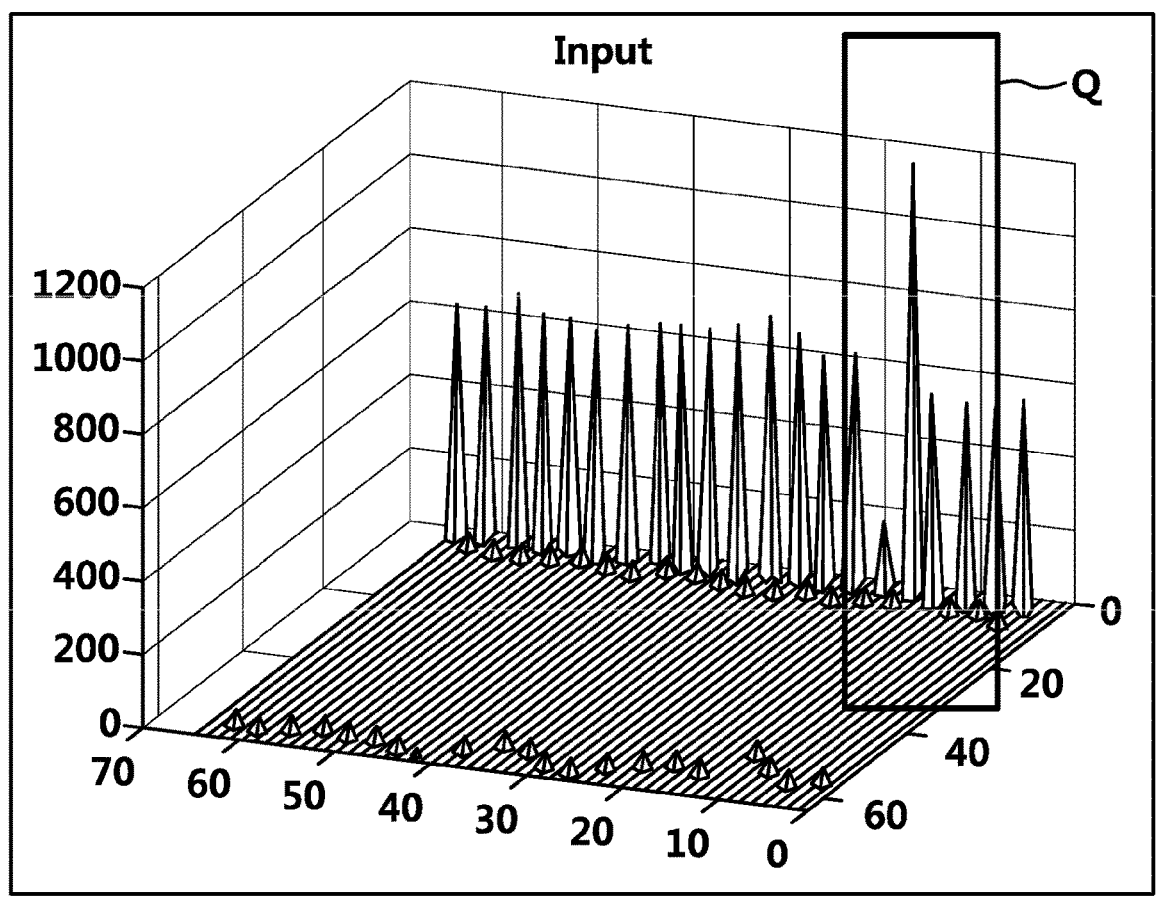
Figure 5B:
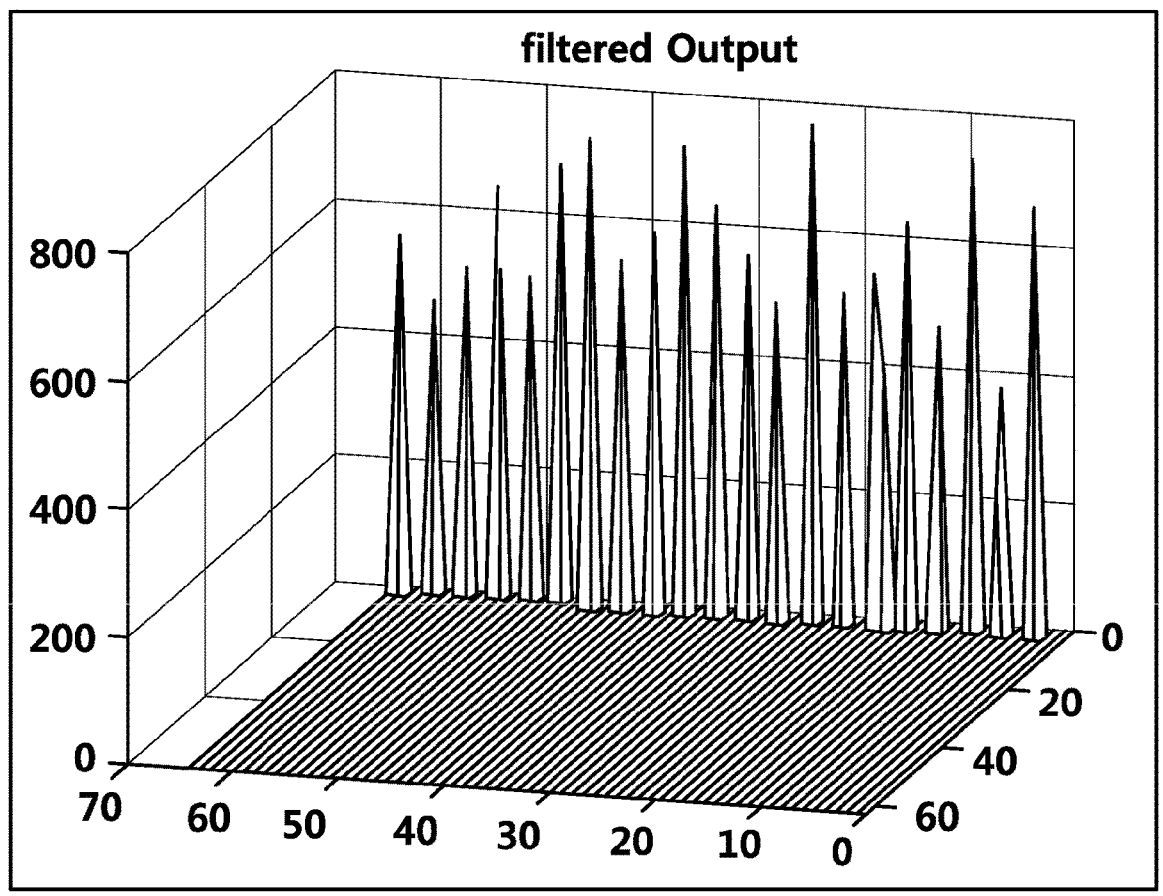

An example of restoration of the diagnostic data is illustrated in FIGS. 5 and 6. In this case, when part of the diagnostic data is lost including the 'Q' part of FIG. 5A, input data is processed similarly to the final data provided through learning with respect to the learned distribution including the mode as illustrated in FIG. 6 and apply it to the lost diagnostic data. As a result, restored diagnostic data is provided as illustrated in FIG. 5B.

Likewise, according to an embodiment of the present invention, it is possible to diagnose the condition of the subject to be measured based on the restored diagnostic data.

Meanwhile, the above-described embodiment illustrates a condition diagnosis performed by signal-processing only a cardiac signal, but other methods are also possible in the present invention.

Figure 7:
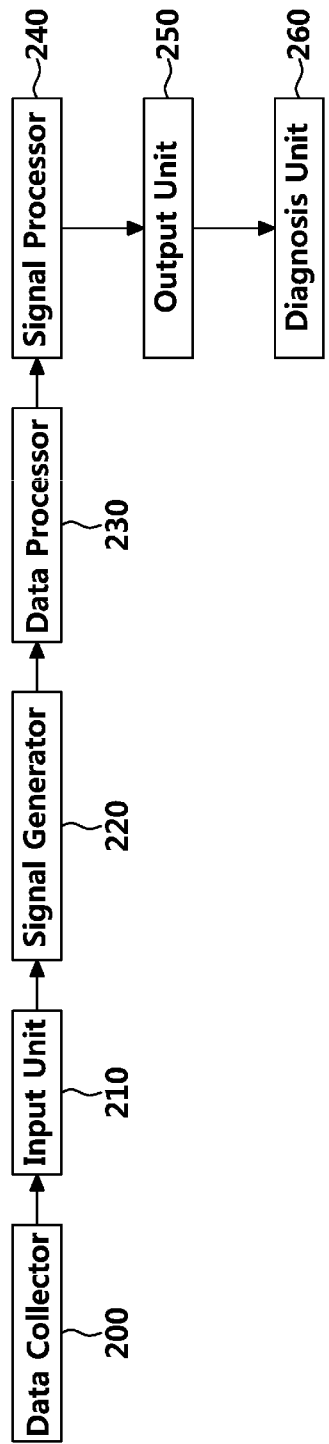
FIG. 7 is a configuration diagram of a cardiac signal processing apparatus according to another embodiment of the present invention.

FIG. 7 is a block diagram of a cardiac signal processing apparatus according to another embodiment of the present invention. In describing other embodiments, detailed descriptions of parts that are the same or similar to the configurations or operations described in the previous embodiments may be omitted.

As illustrated, the cardiac signal processing apparatus includes a data collector 200 for collecting sensor signals (cardiac-related signals) and an input unit 210 for receiving the collected sensor signals.

Further, the cardiac signal processing apparatus includes a signal generator 220 that generates a waveform or function similar in shape to a cardiac signal for the received sensor signal. In the case of the input sensor signal, unnecessary noise may be included, and if noise is included, it may be interpreted as a signal having a shape different from that of the cardiac signal, or the condition cannot be accurately diagnosed due to the noise itself. Therefore, it is to enhance the characteristics of the cardiac signal for an accurate diagnosis.

Further, the cardiac signal processing apparatus includes a data processor 230 for processing data necessary for actual diagnosis from the generated signal. The data processor 230 processes data by using a waveform or function generated by the signal generator 220. The processed data is referred to as processed data.

In addition, the cardiac signal processing apparatus includes a signal processor 240 for processing the signal by performing a learning using a predetermined neural network to the processed data. The signal processor 240 may be referred to as a neural network model that compares the processed data and reference data (e.g., electrocardiogram data) and perform learning until it is determined that the processed data and the reference data are the same. Here, the neural network model may be a generative adversarial network. In other words, it is to signal-process a data with low accuracy of biometric information to a level where accurate condition diagnosis is possible.

In addition, the cardiac signal processing apparatus may further include an output unit 250 for processing and outputting information when information is lost during processing by the signal processor 240. Further, it also includes a diagnosis unit 260 for diagnosing a condition of a subject to be measured based on an output signal of the output unit 250.

As described above, according to another embodiment of the present invention, a diagnosis of condition may be performed by applying a neural network model not only to the original sensor signal but also a signal having enhanced characteristics of the sensor signal, and a process thereof will be described.

Figure 8:
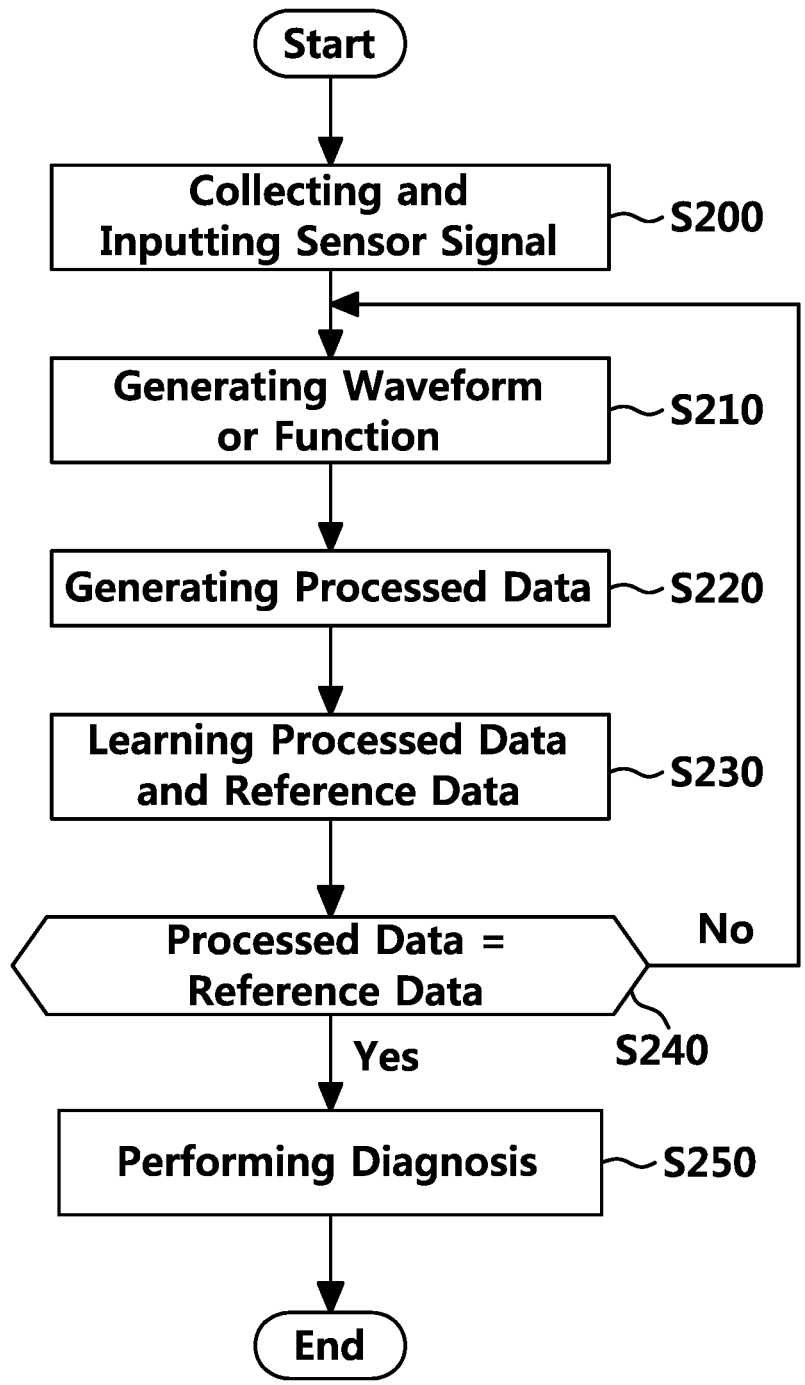
FIG. 8 illustrates a flow chart of cardiac signal processing method according to another embodiment of the present invention.

FIG. 8 is a flowchart illustrating a cardiac signal processing method according to another embodiment of the present invention.

The data collector 200 collects a cardiac-related signal by using a contact sensor and a non-contact sensor, and is input through the input unit 210 (S200). The input signals may contain relatively various noises or other biometric information, and therefore, it can be considered that it is difficult to accurately diagnose the condition with only such input signals. In some cases, it may be determined that a signal pattern completely different from a cardiac signal pattern is input. For such a reason, it is necessary to provide a signal similar to the cardiac signal. The signal generator 220 generates a waveform or function similar in shape to the cardiac signal from the cardiac-related signal including noise (S210). In other words, it may be regarded as a process of reinforcing the characteristics so that the characteristics of the cardiac signal appear. In addition, the data processor 230 generates data necessary for actual diagnosis by using the generated waveform or function (S220).

When data necessary for actual diagnosis is generated as described above, the signal processor 240 compares the processed data generated by the data processor 230 with the reference data, and a learning process is performed until the processed data and the reference data become the same as a result of the comparison. (S230, S240). The learning process is a process in which the signal generator 220 generates a waveform or a function, and a processed data is formed by using the same, and then compared with reference data, and the process is repeatedly performed until it is determined that the two data are identical to each other. Alternatively, even if the two data are not the same, it may be performed until the processed data reaches a threshold value preset by a user. On the other hand, if the comparison result is that the processed data and the reference data are not the same, the process returns to step S210 of generating the waveform or function, and the subsequent process is repeatedly performed.

When such a learning process is completed, the signal processor 240 may output diagnostic data with improved accuracy through the output unit 250. Then, the diagnosis unit 260 diagnoses the condition of the subject to be measured by using the output diagnostic data (S250).

As described above, in the present invention, the accuracy of biosignals required for diagnosis is improved by applying a neural network model to raw data measured by various sensors or to waveforms or function signals that enhance characteristics of the raw data.

Although described with reference to the illustrated embodiments of the present invention as described above, these are only exemplary, and it will be apparent for those of ordinary skill in the art to which the present invention pertains that variations, modifications and other equivalent embodiments are possible, without departing from the gist and scope of the present invention. Therefore, the true technical protection scope of the present invention should be determined by the technical spirit of the appended claims.

Therefore, other implementations, other embodiments, and claims and equivalents are within the scope of the claims to be described.

What is claimed is:

1. Apparatus for cardiac signal processing comprising:
    an input signal processor for extracting data necessary for cardiac diagnosis from a sensor signal of a radar sensor measured in a non-contact state by processing into an electrocardiogram signal that is an electric signal;
    a signal processor for performing learning to detect a heart rate variability per minute using a generative adversarial network algorithm for comparing extraction data extracted by the input signal processor with a reference data;
    an output signal processor for outputting, by using the heart rate variability per minute learned by the signal processor, either of:
        an analysis parameter based on heart rate variability analysis, or
        a signal processed into a waveform of an electrocardiogram signal; and
    a diagnostic unit for diagnosing a heart condition using the analysis parameters or signals processed into the waveform of the electrocardiogram signal, wherein
    the generative adversarial network is a learning model comprising:
        a discriminator network; and
        a generator network.

2. The apparatus of claim 1, wherein the extraction data is an electrocardiogram signal measured by a contact sensor.

3. The apparatus of claim 1, wherein the extraction data is biometric information obtained by restoring a distorted signal included in the sensor signal of the radar sensor.

4. The apparatus of claim 1, wherein the input signal processor performs learning until a P waveform of the electrocardiogram signal is obtained from the extraction data.

5. The apparatus of claim 1, wherein
    the sensor signal of the radar sensor comprises other biometric information and noise in addition to a cardiac signal, and
    the input signal processor removes the other biometric information and noise.

6. The apparatus of claim 1, wherein the output signal processor:
    determines loss and distortion of data from a result of learning of the signal processor, and
    restores data based on a result of the determination.

7. A method for cardiac signal processing, comprising:
    extracting, by an input signal processor, data necessary for cardiac diagnosis from a sensor signal of a radar sensor measured in a non-contact state;
    performing learning, by a signal processor, to detect a heart rate variability per minute using a generative adversarial network algorithm for comparing extraction data extracted by the input signal processor with a reference data;
    outputting, by an output signal processor, by using the heart rate variability per minute learned by the signal processor, either of:
        an analysis parameter based on heart rate variability analysis, or
        a signal processed into a waveform similar to an electrocardiogram signal; and
    diagnosing a heart condition using the analysis parameters or signals processed into the waveform of the electrocardiogram signal, wherein
    the generative adversarial network is a learning model comprising:
        a discriminator network; and
        a generator network.

8. The method of claim 7, wherein the extraction data is an electrocardiogram signal measured by a contact sensor or biometric information obtained by restoring a distorted signal included in the sensor signal of the radar sensor.

9. The method of claim 7, wherein the input signal processor performs learning until a P waveform of the electrocardiogram signal is obtained from the extraction data.

10. The method of claim 7, wherein
    the sensor signal of the radar sensor comprises other biometric information and noise in addition to a cardiac signal, and
    the input signal processor removes the other biometric information and noise.

* * * * *